United States Patent [19]

Oine et al.

[11] Patent Number: 4,794,186
[45] Date of Patent: * Dec. 27, 1988

[54] THIAZOLYLACETIC ACID DERIVATIVE AND PROCESSES FOR PREPARING THE SAME

[75] Inventors: Toyonari Oine, Nara; Yoshihisa Yamada, Kyoto; Hiroshi Sugano, Nara, all of Japan

[73] Assignee: Tanabe Seiyaku Co., Ltd., Osaka, Japan

[ * ] Notice: The portion of the term of this patent subsequent to Jul. 2, 2003 has been disclaimed.

[21] Appl. No.: 681,252

[22] Filed: Dec. 13, 1984

[30] Foreign Application Priority Data

Dec. 21, 1983 [JP] Japan ................. 58-242777

[51] Int. Cl.⁴ ............................................ C07D 417/12
[52] U.S. Cl. .................................... 546/209; 548/194; 548/195
[58] Field of Search ................. 548/194, 195; 546/209

[56] References Cited

U.S. PATENT DOCUMENTS 4,529,802 7/1985 Takaya et al. ............... 548/194
4,547,494 10/1985 Oine et al. .................. 548/194
4,598,075 7/1986 Oine et al. .................. 548/194
4,598,154 7/1986 Oine ........................... 548/198
4,742,174 5/1988 Oine ........................... 546/209

FOREIGN PATENT DOCUMENTS 469277 8/1968 Japan ...................... 548/215
2068957 8/1981 United Kingdom ........ 548/194

Primary Examiner—Robert Gerstl
Attorney, Agent, or Firm—Birch, Stewart, Kolasch & Birch

[57] ABSTRACT

Novel thiazolylacetic acid derivative of the formula:

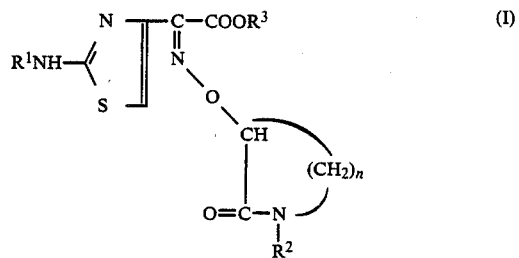

wherein $R^1NH-$ is amino or a protected amino group, $R^2$ is hydrogen or lower alkyl, $-COOR^3$ is carboxy or a protected carboxy group and n is an integer of 2 or 3, and processes for preparing the same. The compound (I) is useful as an intermediate in the synthesis of cephalosporins.

8 Claims, No Drawings

THIAZOLYLACETIC ACID DERIVATIVE AND PROCESSES FOR PREPARING THE SAME

This invention relates to a novel thiazolylacetic acid derivative of the formula:

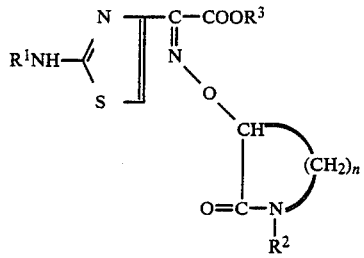
(I)

wherein $R^1NH-$ is amino or a protected amino group, $R^2$ is hydrogen or lower alkyl, $-COOR^3$ is carboxy or a protected carboxy group and n is an integer of 2 or 3, or a salt thereof, and processes for preparing the same.

The compound (I) or a salt thereof of the present invention is novel and is seful as an intermediate in the synthesis of cephalosporins.

Among the compounds of the present invention, a preferred subgenus includes those of the formula (I) in which $R^1$ is hydrogen, lower alkanoyl such as formyl, acetyl or pivaloyl, mono-, di- or trihalogeno-lower alkanoyl such as chloroacetyl or trifluoroacetyl, lower alkoxycarbonyl such as methoxycarbonyl, ethoxycarbonyl or tert.-butoxycarbonyl, mono-, di- or trihalogeno-lower alkoxycarbonyl such as 2,2,2-trichloroethoxycarbonyl, substituted or unsubstituted benzyloxycarbonyl such as benzyloxycarbonyl or p-methoxybenzyloxycarbonyl, substituted or unsubstituted phenyl-lower alkyl such as benzyl, p-methoxybenzyl or 3,4-dimethoxybenzyl, or di- or triphenyl-lower alkyl such as benzhydryl or trityl; $R^2$ is hydrogen or lower alkyl such as methyl, ethyl or propyl; $R^3$ is hydrogen, lower alkyl such as methyl or tert.-butyl, substituted or unsubstituted phenyl-lower alkyl such as benzyl, p-methoxybenzyl or p-nitrobenzyl, or benzhydryl; and n is an integer of 2 or 3. More preferred subgenus includes those of the formula (I) in which $R^1$ is hydrogen, formyl, acetyl, chloroacetyl, 2,2,2-trichloroethoxycarbonyl, benzyloxycarbonyl, or trityl; $R^2$ is hydrogen or methyl; $R^3$ is hydrogen or ethyl; and n is an integer of 2 or 3. Other preferred subgenus includes those of the formula (I) in which $R^1$ is hydrogen, formyl, acetyl, chloroacetyl, 2,2,2-trichloroethoxycarbonyl, benzyloxycarbonyl or trityl, $R^2$ and $R^3$ are hydrogen and n is an integer of 2. Another preferred subgenus includes those of the formula (I) in which $R^1$ is hydrogen or trityl, $R^2$ and $R^3$ are hydrogen and n is an integer of 2. Most preferred subgenus includes those of the formula (I) in which $R^1$, $R^2$ and $R^3$ are hydrogen and n is an integer of 2. In addition, the structural formula (I) shown above intends to show that the isomeric configuration of the oxyimino group is Z (i.e., syn)-configuration. Although the Z (i.e., syn)-isomers of the invention are preferred, they may coexist with small amount of E (or anti)-isomer. Moreover, while the compound (I) can exist in the form of two optical isomers due to asymmetric carbon atom involved therein, either an optical isomer of the compound (I) or a racemic modification thereof are included within the scope of the present invention.

Among said isomers, however, the (Z)-(S)-isomer of the compound (I) is preferred.

According to the present invention, the compound (I) may be prepared by the step(s) of:
reacting a compound of the formula:

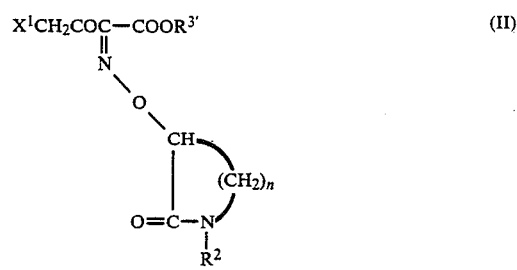
(II)

wherein $-COOR^{3'}$ is carboxy or a protected carboxy group, $X^1$ is halogen and $R^2$ and n are the same as defined above, with a compound of the formula:

$$R^{1'}NH-CSNH_2 \qquad (III)$$

wherein $R^{1'}NH-$ is amino or a protected amino group to give a compound of the formula:

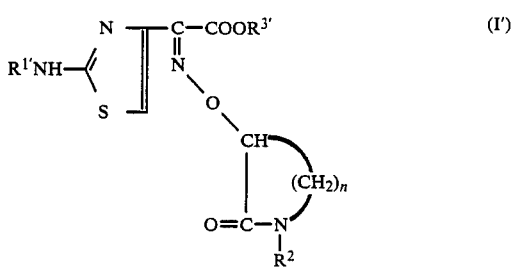
(I')

wherein $R^{1'}NH-$, $R^2$, $-COOR^{3'}$ and n are the same as defined above, or
reacting a compound of the formula:

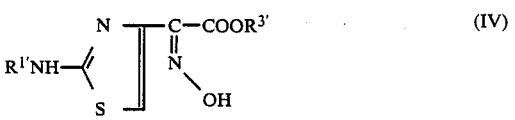
(IV)

wherein $R^{1'}NH-$ and $-COOR^{3'}$ are the same as defined above, with a compound of the formula:

(V)

wherein $X^2$ is a reactive residue and $R^2$ and n are the same as defined above, to give the compound (I'), and if required, removing the protecting group or groups from the compounds (I').

In the above-mentioned reactions, examples of the group represented by $R^{1'}$ include hydrogen, lower alkanoyl such as formyl, acetyl or pivaloyl, mono-, di- or trihalogenolower alkanoyl such as chloroacetyl or trifluoroacetyl, lower alkoxycarbonyl such as methoxycarbonyl, ethoxycarbonyl or tert.-butoxycarbonyl, mono-, di- or trihalogeno-lower alkoxycarbonyl such as 2,2,2-trichloroethoxycarbonyl, substituted or unsubstituted benzyloxycarbonyl such as benzyloxycarbonyl or p-methoxybenzyloxycarbonyl, substituted or unsubstituted phenyl-lower alkyl such as benzyl, p-methoxybenzyl or 3,4-dimethoxybenzyl, and di- or triphenyl-lower alkyl such as benzhydryl or trityl; and examples of the group represented by $R^{3'}$ include hydrogen, lower alkyl such as methyl, ethyl or tert.-butyl, substituted or unsubstituted phenyl-lower alkyl such as benzyl, p-methoxybenzyl or p-nitrobenzyl, and benzhydryl. Examples of the reactive residue ($X^2$) include a group of the formula: $R^4SO_2O-$ (wherein $R^4$ lower alkyl or an unsubstituted or substituted phenyl) (e.g., methylsulfonyloxy, ethylsulfonyloxy, phenylsulfonyloxy, p-tosyloxy) and halogen atom (e.g., chlorine, bromine).

The reaction of the compound (II) with the compound (III) may be accomplished in the presence of an acid acceptor in a solvent. The acid acceptor includes, for example, an organic tertiary amine such as N,N-dimethylaniline, triethylamine or pyridine. Lower alkanol (e.g., methanol, ethanol, isopropanol) or a mixture of said alkanol and water is suitable as the solvent. It is preferred to carry out hhe reaction at a temperature of 10° C. to 80° C.

The reaction of the compound (IV) with the compound (V) may also be accomplished in the presence of an acid acceptor in a solvent. The acid acceptor includes, for example, an alkali metal carbonate (e.g., potassium carbonate, sodium carbonate), an alkali metal hydride (e.g., sodium carbonate, sodium carbonate), an alkali metal hydride (e.g., sodium hydride), or an alkali metal hydroxide (e.g., sodium hydroxide, potassium hydroxide). Acetone, tetrahydrofuran, ethyl acetate, dimethylsulfoxide and dimethylformamide are suitable as the solvent. It is preferred to carry out the reaction at a temperature of 10° C. to 80° C.

The removal of the protecting group or groups from the compound (I') thus obtained may be conducted by conventional manners such as, for example, hydrolysis, solvolysis, acid treatment or reduction. For example, when the protecting group ($R^{1'}$) on the amino group is formyl, acetyl, tert.-butoxycarbonyl, benzhydryl or trityl and the protecting group ($R^{3'}$) on the carboxy group is tert.-butyl or benzhydryl, said group or groups may be removed by treating the compound (I') with an acid. Suitable examples of such acid include formic acid, trifluoroacetic acid, benzenesulfonic acid, p-toluenesulfonic acid, hydrochloric acid or hydrogen bromide. This reaction may be conducted with or without a solvent. Examples of the solvent are water, methanol, ethanol, acetic acid or dioxane. It is preferred to carry out the reaction at a temperature of −30° C. to 70° C., especially 10° C. to 50° C. Moreover, when the trifluoroacetic acid is used as the acid, it is preferred to carry it out in the presence of anisole. When the protecting group ($R^{1'}$) on the amino group is trityl, the removal of said protecting group may be conducted by heating the compound (I') in a solvent. Suitable examples of the solvent are lower alkanol (e.g., methanol, ethanol), water or a mixture thereof. It is preferred to carry out the reaction at a temperature of 40° C. to 100° C., preferably at 50° C. to 80° C. When the protecting group ($R^{1'}$) on the amino group is benzyloxycarbonyl, p-methoxybenzyloxycarbonyl, benzyl, p-methoxybenzyl or 3,4-dimethoxybenzyl and the protecting group ($R^{3'}$) on the carboxy group is benzyl, p-methoxybenzyl or p-nitrobenzyl, the removal of said potecting group or groups may be conducted by catalytic hydrogenation of the compound (I') in hydrogen gas in the presence of a catalyst. This catalytic hydrogenation is preferably carried out at a temperature of 0° C. to 100° C., especially 10° C. to 40° C., under atmospheric or increased pressure. Preferred examples of the catalyst include palladium-$BaCO_3$, palladium-charcoal and palladium-black. Methanol, ethanol, tetrahydrofuran and water are suitable as the reaction solvent. Further, when the protecting group ($R^{1'}$) on the amino group is trifluoroacetyl, pivaloyl, methoxycarbonyl or ethoxycarbonyl and the protecting group ($R^{3'}$) on the carboxy group is lower alkyl such as methyl or ethyl, said group or groups may be removed by hydrolysis of the compound (I'). The hydrolysis of the compound (I') may be carried out in conventional manners, for example, by treating it with an alkali agent or an acid in a solvent. Examples of the alkali agent include an alkali metal hydroxide (e.g., sodium hydroxide, potassium hydroxide), or an alkali earth metal hydroxide (e.g., calcium hydroxide, ballium hydroxide), and examples of the acid include hydrochloric acid and hydrobromic acid. Lower alkanol (e.g., methanol, ethanol), dimethylformamide and a mixture of said solvent and water are suitable as the solvent. It is preferred to carry out the reaction at a temperature of 10° C. to 80° C. preferably at 20° C. to 60° C. When the protecting group ($R^{1'}$) on the amino group is chloroacetyl, said group may be removed by treating the compound (I') with thiourea in a solvent. Methanol, ethanol and water are suitable as the solvent. It is preferred to carry it out at a temperature of 20° C. to 80° C., especially 20° C. to 50° C.

The starting compound (II) or (V) of the present invention involves two optical isomers due to asymmetric carbon atom involved therein. However, since all of the above-mentioned reactions of the invention can be carried out without racemization, the compound (I) of the invention in an optically active form can be readily obtained by the use of an optically active isomer of the compound (II) of (V) as the starting material.

On the other hand, when the compound (I) is in the form of racemic modification, the compound (I) may be resolved into each optically active enantiomers by using a resolving agent. Namely, an optically active isomer of the compound (I) in which $-COOR^3$ is carboxy group may be prepared by reacting a racemic modification of the compound (I) ($R^3$=H) with an optically active resolving agent selected from the group consisting of an optically active tyrosine hydrazide, an optically active α-methylbenzylamine and an optically active phenylalanine lower alkyl ester to form two diastereoisomeric salts thereof, separating said diastereoisomeric salts from each other by difference in solubility thereof, and converting the separated salt into its free acid.

To illustrate more specifically, the racemic modification of the compound (I) in which $R^1NH-$ is amino group, $R^2$ is hydrogen, $-COOR^3$ is carboxy group and n is an integer of 2, i.e., (Z)-2-(2-aminothiazol-4-yl)-2-[((3RS)-2-pyrrolidon-3-yl)oxyimino]acetic acid, can be readily separated into each optical isomers by the steps of reacting said compound with an optically active tyrosine hydrazide to form two diastereoisomeric salts thereof, and separating said diastereoisomeric salts from each other by difference in solubility thereof. (Z)-2-(2-aminothiazol-4-yl)-2-[((3S)-2-pyrrolidon-3-yl)oxyimino]acetic acid forms the less soluble diastereoisomeric salt if L-tyrosine hydrazide is used as the resolving agent, and, on the other hand, (Z)-2-(2-aminothiazol-4-yl)-2-[((3R)-2-pyrrolidon-3-yl)oxyimino]acetic acid forms the less soluble diastereoisomeric salt if D-tyrosine hydrazide is used as the resolving agent. The compound (I) in which R¹NH— is tritylamino group, R² is hydrogen, —COOR³ is carboxy and n is an integer of 2, i.e., (Z)-2-(2-tritylaminothiazol-4-yl)-2-[((3RS)-2-pyrrolidon-3-yl)oxyimino]acetic acid, can be readily separated into each optical isomers by the steps of reacting said compound with an optically active phenylalanine lower alkyl ester (e.g., methyl ester) or an optically active α-methylbenzylamine to form two diastereoisomeric salts thereof, and separating said diastereoisomeric salts from each other by difference in solubility thereof. (Z)-2-(2-tritylaminothiazol-4-yl)-2-[((3S)-2-pyrrolidon-3-yl)oxyimino]acetic acid forms the less soluble diastereoisomeric salt if L-phenylalanine ester or (+)-α-methylbenzylamine is used as the resolving agent, and, on the other hand, (Z)-2-(2-tritylaminothiazol-4-yl)-2-[((3R)-2-pyrrolidon-3-yl)oxyimino]acetic acid forms the less soluble diastereoisomeric salt if D-phenylalanine ester or (−)-α-methylbenzylamine is used as the resolving agent.

In the above-mentioned reaction of the compound (I) with the resolving agent, said resolving agent is preferably used at an amount of 0.5 to 1.3 moles, especially 0.8 to 1.3 moles, per mole of the racemic modification of the compound (I). It is preferred to carry out the reaction at a temperature of 0° C. to 70° C. in a solvent (e.g., water, a lower alkanol such as methanol or ethanol, a lower alkanone such as acetone, dioxane, tetrahydrofuran or a mixture thereof). The subsequent separation of the diastereoisomeric salts from each other is carried out by crystallizing the less soluble diastereoisomeric salt, and then collecting said less soluble distereoisomeric salt from the reaction mixture according to a conventional solid-liquid separation technique such as filtration or centrifugation. The less soluble diastereoisomeric salt thus obtained may be, if necessary, subjected to a further treatment such as washing or recrystallization.

The less soluble diastereoisomeric salt thus obtained can readily be converted to the optically active compound (I) in free form by treating the thus-obtained diastereoisomeric salt with an acid (e.g., hydrochloric acid, sulfuric acid), or by subjecting the diastereoisomeric salt to salt exchange reaction with an amine (e.g., diethylamine, triethylamine, piperazine, pyridine, N-methylmorpholine), and then treating the resultant amine salt with an acid.

The thus-obtained compound (I) of the present invention in which R¹NH— is amino group and/or —COOR³ is carboxy may be converted to the salt thereof by a conventional method. Examples of such salts include, for example, metalic salts such as sodium, potassium, calcium or aluminum salts; ammonium salt; salts thereof with amines such as diethylamine or triethylamine; salts thereof with pyridine, piperazine or N-methylmorpholine; salts thereof with inorganic acids such as hydrochloric acid, hydrobromic acid, sulfuric acid or nitric acid; salts thereof with organic acids such as benzensulfonic acid, methanesulfonic acid or p-toluenesulfonic acid.

The compound (I) of the present invention is useful as an intermediate in the synthesis of cephalosporin compounds. For example, a cephalosporin compound of the formula:

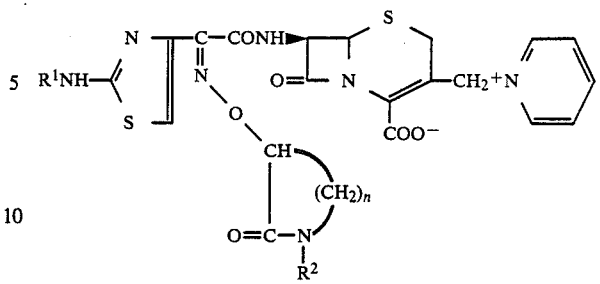

wherein R¹NH—, R² and n are the same as defined above, as disclosed in U.S. patent application Ser. No. 516,053 or European Patent Application No. 83304527, is prepared by condensing the compound (I) with a compound of the formula:

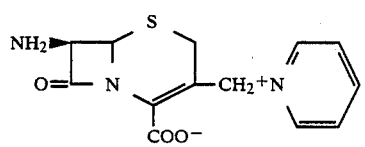

and, if required, further removing the protecting group from the resultant compound. Said cephalosporin compound shows an excellent antimicrobial activity upon either gram-positive or gram-negative bacteria as compared with known cephalosporin compounds. For example, the (S)-isomer of the above-mentioned cephalosporin compound in which R¹NH— is amino group, R² is hydrogen and n is an integer of 2, i.e., (6R, 7R)-7-{(Z)-2-(2-aminothiazol-4-yl)-2-[((3S)-2-pyrrolidon-3-yl)oxyimin]acetamido}-3-(1-pyridiniomethyl)-3-cephem-4-carboxylate, exhibits the minimum inhibitory concentration (M.I.C.) (Agar dilution method, cultured for 20 hours at 37° C.) of 12.5 μg/ml against Streptococcus faecalis CN 478, while the M.I.C. of Cefmenoxime [Chemical name: 7β-[(Z)-2-(2-aminothiazol-4-yl)-2-(methoxyimino)acetamido]-3-[(1-methyl-1H-tetrazol-5-yl)thiomethyl]-3-cephem-4-carboxilic acid] and Ceftazidime [Chemical name: 7β-[(Z)-2-(2-aminothiazol-4-yl)-2-(2-carboxyprop-2-yloxyimino)acetamido]-3-(1-pyridiniomethyl)-3-cephem-4-carboxylate] against said microorganism are more than 100 μg/ml. Further, (6R,7R)-7-{(Z)-2-(2-aminothiazol-4-yl)-2-[((3S)-2-pyrrolidon-3-yl)oxyimino]acetamido}-3-(1-pyridiniomethyl)-3-cephem-4-carboxylate exhibits the M.I.C. of 0.39 μg/ml against Pseudomonas aeruginosa.

The starting compound (IV) may be prepared, for example, according to the method described in Tetrahedron., Vol. 34, pages 2233–2243(1978).

On the other hand, the starting compound (II) is novel and may be prepared according to the method shown by the following reaction scheme:

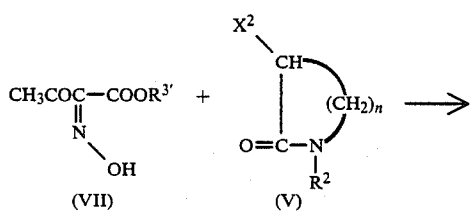

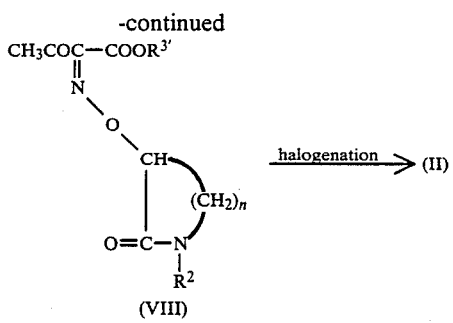

(VIII)

wherein $R^2$, —$COOR^{3'}$, $X^2$ and n are the same as defined above.

Namely, the compound (II) may be prepared by reacting the compound (VII) with the compound (V) to give the compound (VIII), followed by halogenation thereof.

The reaction of the compound (VII) with the compound (V) may be accomplished in the presence of an acid acceptor in a solvent. Examples of the acid acceptor include an alkali metal carbonate (e.g., potassium carbonate, sodium carbonate), an alkali metal hydride (e.g., sodium hydride) and an alkali metal hydroxide (e.g., sodium hydroxide, potassium hydroxide). Acetone, tetrahydrofuran, ethyl acetate, dimethylsulfoxide and dimethylformamide are suitable as the solvent. It is preferred to carry out the reaction at a temperature of 10° C. to 50° C.

The subsequent halogenation may be accomplished in a solvent. Examples of a halogenating agent which may be used for this reaction include sulfuryl chloride, chlorine, bromine, N-bromosuccinimide or pyridiniumhydrobromide perbromide. Chloroform, methylene chloride, carbon tetrachloride and 1,2-dichloroethane are suitable as the solvent. It is preferred to carry out the reaction at a temperature of 10° C. to 50° C.

All of the aforementioned reactions may be carried out without racemization.

The optically active isomer of the compound (V) in which $X^2$ is a group of the formula: $R^4SO_2O$— (wherein $R^4$ is the same as defined above) may be prepared, for example, by treating the optically active 3-hydroxy-2-pyrrolidon (cf. Acta Chemica Scandinavica., B 34, pages 731–733, (1980)) with a compound of the formula: $R^4SO_2X^3$ (wherein $X^3$ is halogen and $R^4$ is the same as defined above).

Practical and presently-preferred embodiments of the present invention are illustratively shown in the following Examples. Throughout the specification and claims, the terms "lower alkyl", "lower alkoxy" and "lower alkanoyl" should be interpreted as referring to alkyl having one to four carbon atoms, alkoxy having one to four carbon atoms and alkanoyl having two to five carbon atoms, respectively. The terms "lower alkanol" and "lower alkanone" should be interpreted as referring to alkanol having one to four carbon atoms and alkanone having 3 to 5 carbon atoms.

EXAMPLE 1

(1) 3.2 g of ethyl 2-hydroxyimino-3-oxo-n-butyrate are dissolved in 25 ml of acetone, and 4.2 g of potassium carbonate and 7.6 g of (R)-3-(p-tosyloxy)-2-pyrrolidone are added thereto. After the mixture is stirred at room temperature for 15 hours, the mixture is concentrated under reduced pressure to dryness. 50 ml of ice-water are added to the residue, and the mixture is extracted with ethyl acetate. The extract is dried and concentrated under reduced pressure to dryness. 3.3 g of ethyl (Z)-2-[((3S)-2-pyrrolidon-3-yl)oxyimino]-3-oxo-n-butyrate are obtained.

NMR (CDCl$_3$)δ: 1.32 (3H, t, J=7 Hz), 2.00 (3H, S) 2.04–2.86 (2H, m), 3.3–3.7 (2H, m) 4.36 (2H, q, J=7 Hz), 4.96 (1H, t, J=7 Hz) 7.5 (1H, broad s).

(2) 2.4 g of ethyl (Z)-2-[((3S)-2-pyrrolidon-3-yl)-oxyimino]-3-oxo-n-butyrate are dissolved in 15 ml of methylene chloride, and 1.6 g of sulfuryl chloride are added thereto. The mixture is stirred at 15° to 25° C. for 20 hours. Then, the mixture is concentrated under reduced pressure to remove solvent. The residue is dissolved in chloroform, and the solution is washed with water. The chloroform solution is dried and concentrated under reduced pressure to dryness. Ethyl (Z)-2-[((3S)-2-pyrrolidon-3-yl)oxyimino]-3-oxo-4-chloro-n-butyrate is thereby obtained as crude product. The crude product thus obtained is dissolved in 20 ml of ethanol, and one g of thiourea and 1.2 g of N,N-dimethylaniline are added thereto. The mixture is stirred at 20° to 25° C. for 2 hours. Then, the mixture is concentrated under reduced pressure to remove solvent. The residue is dissolved in chloroform, and the solution is washed with water and an aqueous sodium bicarbonate solution, successively. The chloroform solution is dried and concentrated under reduced pressure to remove solvent. The residue is crystallized with isopropanol, and the crystals are collected by filtration. 1.2 g of ethyl (Z)-2-(2-aminothiazol-4-yl)-2-[((3S)-2-pyrrolidon-3-yl)oxyimino]acetate are obtained.

M.p. 160°–163° C.

[α]$_D^{25}$: −15.9° (c=1, methanol).

NMR (DMSO-d$_6$)δ: 1.27 (3H, t, J=7 Hz), 1.93–2.60 (2H, m), 3.1–3.5 (2H, m), 4.32 (2H, q, J=7 Hz), 4.74 (1H, t, J=7 Hz), 6.93 (1H, s), 7.30 (2H, s), 7.96 (1H, s).

(3) 0.27 g of sodium hydroxide is dissolved in a mixture of 3 ml of methanol and one ml of water, and one g of ethyl (Z)-2-(2-aminothiazol-4-yl)-2-[((3S)-2-pyrrolidon-3yl)oxyimino]acetate is added thereto. The mixture is stirred at 20° C. for one hour to dissolve said acetate therein. The solution is adjusted to pH 5 with 10% hydrochloric acid, and the aqueous mixture is concentrated under reduced pressure to remove methanol. The residue is adjusted to pH 3 with 10% hydrochloric acid, and the aqueous mixture is ice-cooled. Crystalline precipitates are collected by filtration, and the crystals are washed with methanol and then dried. 730 mg of (Z)-2-(2-aminothiazol-4-yl)-2-[((3S)-2-pyrrolidon-3-yl)oxyimino]acetic acid are obtained.

M.p. 199°–200° C. (decomp.).

[α]$_D^{25}$: −50.8° (C=1, water).

NMR (D$_2$O+NaHCO$_3$)δ: 2.0–2.7 (2H, m), 3.3–3.6 (2H, m), 4.95 (1H, t, J=8 Hz), 6.90 (1H, s).

EXAMPLE 2

(1) 31.8 g of ethyl 2-hydroxyimino-3-oxo-n-butyrate are dissolved in 150 ml of acetone, and 83 g of anhydrous potassium carbonate are added thereto. 33 g of 3-bromo-2-pyrrolidone are added to the mixture at 20° to 25° C. with stirring, and the mixture is stirred at the same temperature for one hour. One liter of ice-water is added to said mixture, and the aqueous mixture is extracted with ethyl acetate. The extract is dried and concentrated under reduced pressure to remove solvent. The residue is crystallized with diisopropyl ether, and the crystals are collected by filtration. The crystals are recrystallized from ethyl acetate. 32 g of ethyl (Z)-2-[(2-pyrrolidon-3-yl)-oxyimino]-3-oxo-n-butyrate are obtained as colorless needles.

M.p. 92°–93° C.

NMR (CDCl$_3$)$\delta$: 1.33 (3H, t, J=8 Hz), 200 (3H, s), 2.05–2.85 (2H, m), 3.3–3.7 (2H, m), 4.37 (2H, q, J=8 Hz), 4.98 (1H, t, J=7 Hz), 7.53 (1H, broad s).

(2) 14.5 g of ethyl (Z)-2-[(2-pyrrolidon-3-yl)oxyimino]-3-oxo-n-butyrate are dissolved in 60 ml of methyl chloride, and 9.6 g of sulfuryl chloride are added thereto. The mixture is stirred at 15° to 25° C. for 40 hours. Then, the mixture is concentrated under reduced pressure to dryness. The residue is dissolved in chloroform, and the solution is washed with water. The chloroform solution is dried and concentrated under reduced pressure to dryness. The residue is crystallized with ether, and the crystals are collected by filtration. The crystals are recrystallized from ethyl acetate. 6.5 g of ethyl (Z)-2-[2-pyrrolidon-3-yl)oxyimino]-3-oxo-4-chloro-n-butyrate are obtained.

M.p. 102°–103° C.

NMR (CDCl$_3$)$\delta$: 1.34 (3H, t, J=7 Hz), 2.0–2.9 (2H, m), 3.3–3.6 (2H, m), 4.39 (2H, q, J=7 Hz), 4.62 (2H, s), 5.20 (1H, t, J=7 Hz), 7.54 (1H, s).

(3) 27.7 g of ethyl (Z)-2- [(2-pyrrolidon-3-yl)-oxyimino]-3-oxo-4-chloro-n-butyrate and 7.6 g of thiourea are added to 200 ml of ethanol, and 20 g of N,N-dimethylaniline are added thereto. The mixture is stirred at 20° to 25° C. for 2 hours. Then, the mixture is concentrated under reduced pressure to dryness. The residue is dissolved in chloroform, and the solution is washed with water and an aqueous sodium bicarbonate solution, successively. The chloroform solution is dried and concentrated under reduced pressure to remove solvent. The residue is cystallized with isopropanol, and the crystals are collected by filtration. 17.5 g of ethyl (Z)-2-(2-aminothiazol-4-yl)-2-[2-pyrrolidon-3-yl)oxyimino]acetate are obtained.

M.p. 156°–158° C.

NMR (DMSO-d$_6$)$\delta$: 1.28 (3H, t, 7 Hz), 1.8–2.6 (2H, m), 3.1–3.5 (2H, m), 4.32 (2H, q, J=7 Hz), 4.77 (1H, t, J=7.5 Hz), 6.93 (1H, s) 7.30 (2H, s), 7.98 (1H, s).

(4) 3.0 g of ethyl (Z)-2-(2-aminothiazol-4-yl)-2-[((2-pyrrolidon-3-yl)oxyimino]acetate are suspended in 60 ml of methanol, and 10 ml of 2N sodium hydroxide are added thereto. The mixture is refluxed for 30 minutes with heating. After cooling, the mixture is neutralized with 20 ml of 1N hydrochloric acid, and the aqueous mixture is concentrated under reduced pressure to dryness. The residue is crystallized with 10 ml of ice-water, and the crystals are collected by filtration and then dried at 70° C. under reduced pressure. 2.2 g of (Z)-2-(2-aminothiazol-4-yl)-2-[(2-pyrrolidon-3-yl)oxyimino]acetic acid are obtained as colorless prisms.

M.p. 158°–159° C. (decomp.).

NMR (DMSO-d$_6$)$\delta$: 1.9–2.7 (2H, m), 3.1–3.4 (2H, m) 4.79 (1H, t, J=7 Hz), 6.90 (1H, s). 7.30 (2H, broad s), 8.00 (1H, s)

EXAMPLE 3

4.9 g of ethyl (Z)-2-[(2-pyrrolidon-3-yl)oxyimino]-3-oxo-n-butyrate are dissolved in 20 ml of methylene chloride, and 2.9 g of sulfuryl chloride are added thereto. The mixture is stirred at 20° to 25° C. for 48 hours. Then, the mixture is concentrated under reduced pressure to remove solvent. The residue is dissolved in chloroform, and the solution is washed with water. The chloroform solution is dried and concentrated under reduced pressure to remove solvent. The residue (4.9 g ) is dissolved in 20 ml of ethanol, and 1.3 g of thiourea and 4 g of N,N-dimethylaniline are added thereto. The mixture is stirred at room temperature for 2 hours. Then, the mixture is concentrated under reduced pressure to dryness. The residue is dissolved in chloroform, and the solution is washed with water and an aqueous sodium bicarbonate solution, successively. The chloroform solution is dried and concentrated under reduced pressure to dryness. The residue is crystallized with isopropanol, and the crystals are collected by filtration. 1.9 g of ethyl (Z)-2-(2-aminothiazol-4-yl)-2-[(2-pyrrolidon-3-yl)oxyimino]acetate are obtained. The physicochemical properties of this product are identical with those of the product obtained in Example 2-(3).

EXAMPLE 4

(1) 2.77 g of ethyl (Z)-2-[(2-pyrrolidon-3-yl)oxyimino]-3-oxo-4-chloro-n-butyrate and 1.2 g of acetylthiourea are added to 20 ml of ethanol, and 2.0 g of N,N-dimethylaniline are added thereto. The mixture is stirred at 20° to 30° C. for 4 hours. Then, the mixture is concentrated under reduced pressure to drynss. The residue is dissolved in chloroform, and the solution is washed with water and an aqueous sodium bicarbonate solution, successively. The chloroform solution is dried and concentrated under reduced pressure to remove solvent. The residue is crystallized with isopropanol, and the crystals are collected by filtration. 1.7 g of ethyl (Z)-2-(2-acetamidothiazol-4-yl)-2-[(2-pyrrolidon-3-yl)oxyimino]acetate are obtained.

M.p. 210°–215° C. (decomp.).

NMR (DMSO-d$_6$)$\delta$: 1.30 (3H, t, J=7 Hz), 1.9–2.4 (2H, m), 2.16 (3H, s), 3.1–3.4 (2H, m), 4.40 (2H, q, J=7 Hz), 4.83 (1H, t, J=7 Hz), 7.56 (1H, s), 8.01(1H, s), 12.51 (1H, s)

(2) 1.7 g of ethyl (Z)-2-(2-acetamidothiazol-4-yl)-2-[(2-pyrrolidon-3-yl)oxyimino]acetate are suspended in 17 ml of methanol, and 5 ml of 2N sodium hydroxide are added thereto. The mixture is refluxed for 30 minutes with heating. Then, the mixture is concentrated under reduced pressure to remove methanol. The residue is adjusted to pH 2 with diluted hydrochloric acid, and the aqueous mixture is extracted with a mixture of ethyl acetate and tetrahydrofuran (2:1). The extract is dried and concentrated under reduced pressure to dryness. The residue is crystallized with isopropanol, and the crystals are collected by filtration and then recrystallized from water. 0.8 g of (Z)-2-(2-acetamidothiazol-4-yl)-2-[(2-pyrrolidon-3-yl)oxyimino]acetic acid is obtained.

M.p. 144° C. (decomp.).

NMR (DMSO-d$_6$)$\delta$: 2.0–2.4 (2H, m), 2.16 (3H, s), 3.1–3.5 (2H, m), 4.81 (1H, t, J=7 Hz), 7.49 (1H, s), 7.99 (1H, s), 12.51 (1H, s).

EXAMPLE 5

(1) 2.42 g of ethyl (Z)-2-[(2-pyrrolion-3-yl)oxyimino]-3-oxo-n-butyrate are dissolved in 10 ml of methylene chloride, and 1.62 g of sulfuryl chloride are added thereto. The mixture is stirred at 15° to 20° C. for 20 hours. Then, the mixture is concentrated under reduced pressure to remove solvent. The residue is dissolved in chloroform, and the solution is washed with water. The chloroform solution is dried an concentrated under reduced pressure to remove solvent. The residue is dissolved in 25 ml of ethanol, and 2.52 g of N-(2,2,2-trichloroethoxycarbonyl)thiourea and 2.53 g of N,N- dimethylaniline are added thereto. The mixture is stirred at room temperature for 30 minutes and then refluxed for one hour with heating. Then, the mixture is concentrated under reduced pressure to dryness. The residue is dissolved in ethyl acetate, and the solution is washed with water, 5% hydrochloric acid, 5% aqueous sodium bicarbonate solution and an aqueous sodium chloride solution, successively. The ethyl acetate solution is dried and concentrated under reduced pressure to remove solvent. The residue is crystallized with ether, and the crystals are collected by filtration. 1.53 g of ethyl (Z)-2- [2-(2,2,2-trichloroethoxycarbonylamino)thiazol-4-yl]-2-[(2-pyrrolidon-3-yl)oxyimino]acetate are obtained.

M.p. 175°–180° C. (decomp.).

NMR (DMSO-$d_6$)$\delta$: 1.30 (3H, t, J=7 Hz), 2.0–2.4(2H, m), 3.1–3.5 (2H, m), 4.40 (2H, q, J=7 Hz), 4.85 (1H, t, J=7 Hz), 5.04 (2H, s), 7.61 (1H, s), 8.00 (1H, s), 12.7 (1H, broad s).

(2) 1.42 g of ethyl (Z)-2-[2-(2,2,2-trichloroethoxycarbonylamino)thiazol-4-yl]-2-[(2-pyrrolidon-3-yl)oxyimino]acetate are suspended in 30 ml of methanol, and 3 ml of 2N sodium hydroxide are added thereto with ice-cooling. The mixture is stirred at room temperature for one hour and then refluxed for 30 minutes with heating. Then, the mixture is concentrated under reduced pressure to dryness. 5 ml of water are added to the residue, and the aqueous mixture is washed with ethyl acetate. The aqueous mixture is adjusted to pH 2 to 3 with diluted hydrochloric acid, and the mixture is extracted with a mixture of ethyl acetate and tetrahydrofuran (2:1). The extract is dried and concentrated under reduced pressure to dryness. The residue is purified by silica gel chromatography (solvent, ethyl acetate:methanol=4:1). 0.4 g of (Z)-2-[(2-(2,2,2-trichloroethoxycarbonyl-amino)thiazol-4-yl]-2-[(2-pyrrolidon-3-yl)oxyimino]acetic acid is obtained. This product begins to gradually decompose at 190° C.

IR$\nu_{max}^{nujol}$ (cm$^{-1}$): 3400, 3250, 1692, 1610, 1517.

UV$\lambda_{max}$ (methanol): 217, 235, 284 nm.

EXAMPLE 6

1.07 g of ethyl (Z)-2-(2-aminothiazol-4-yl)-2-hydroxyiminoacetate are dissolved in 5 ml of dimethylsulfoxide, and one g of potassium carbonate and 1.53 g of (R)-3-(p-tosyloxy)-2-pyrrolidone are added thereto. The mixture is stirred at room temperature overnight. Water is added to the reaction mixture, and the aqueous mixture is extracted with chloroform. The extract is washed with water, dried and then concentrated under reduced pressure to dryness. The residue is crystallized with isopropyl ether, and the crystals are recrystallized from aqueous methanol. 0.86 g of ethyl (Z)-2-(2-aminothiazol-4-yl)-2-[((3S)-2-pyrrolidon-3-yl)oxyimino]acetate is obtained. The physico-chemical properties of this product are identical with those of the product obtained in Example 1-(2).

EXAMPLE 7

10.9 g of ethyl (Z)-2-(2-aminothiazol-4-yl)-2-hydroxyiminoacetate are dissolved in 25 ml of dimethylsulfoxide, and a solution of 14 g of anhydrous potassium carbonate in 13 ml of water is added thereto at a temperature of 15° to 20° C. The mixture is stirred at the same temperature for 20 minutes. 10 g of 3-bromo-2-pyrrolidone are added to said mixture at room temperature, and the mixture is stirred at the same temperature for 1.5 hours. 120 ml of water are added to the reaction mixture, and the aqueous mixture is stirred with ice-cooling. Crystalline precipitates are collected by filtration, and the crystals are washed with water and then dried at 40° C. 13 g of ethyl (Z)-2-(2-aminothiazol-4-yl)-2-[(2-pyrrolidon-3yl)oxyimino]acetate are obtained. The physico-chemical properties of this product are identical sith those of the product obtained in Example 2-(3).

EXAMPLE 8

(1) 15.8 g of ethyl (Z)-2-(2-tritylaminothiazol-4-yl)-2-hydroxyiminoacetate are dissolved, in 70 ml of dimethylsulfoxide, and 5.8 g of anhydrous potassium carbonate are added thereto. The mixture is stirred at room temperature for 20 minutes. 6.6 g of 3-bromo-2-pyrrolidone are added to said mixture, and the mixture is stirred at room temperature for 20 hours. The mixture is poured into 800 ml of water, and crystalline precipitates are collected by filtration and washed with water. The crystals are dissolved in chloroform, washed with water and then dried. Then, the chloroform solution is evaporated under reduced pressure to remove solvent. 100 ml of ethyl acetate are added to the residue, and allowed to stand at room temperature. Crystalline precipitates thus obtained are collected by filtration and dried. 16.0 g of ethyl (Z)-2-(2-tritylaminothiazol-4-yl)-2-[(2-pyrrolidon-3-yl)oxyimino]acetate are obtained.

M.p. 209°–210° C.

NMR (CDCl$_3$)$\delta$: 1.30 (3H, t, J=7 Hz), 2.1–2.6 (2H, m), 3.1–3.6 (2H, m), 4.34 (2H, q, J=7 Hz), 4.90 (1H, t, J=7 Hz), 6.53 (1H, s), 7.0–7.6 (17H, m).

(2) 16.0 g of ethyl (Z)-2-(2-tritylaminothiazol-4-yl)-2-[(2-pyrrolidon-3-yl)oxyimino]acetate are added to a mixture of 160 ml of methanol and 30 ml of an aqueous 2N sodium hydroxide solution, and the mixture is refluxed for 30 minutes under heating. After cooling, crystalline precipitates are collected by filtration and washed with methanol. The crystals are suspended in 30 ml of water. Then, the suspension is adjusted to pH 3 with 2N hydrochloric acid. Crystalline precipitates are collected by filtration and dried. 11.4 g of (Z)-2-(2-tritylaminothiazol-4-yl)-2-[(2-pyrrolidon-3-yl)oxyimino]acetic acid are obtained.

M.p. 150°–153° C. (decomp.).

NMR (DMSO-$d_6$)$\delta$: 1.8–2.4 (2H, m), 2.9–3.4 (2H, m), 4.63 (1H, t, J=7 Hz), 6.76 (1H, s), 6.9–7.6 (15H, m), 7.85 (1H, s), 8.70 (1H, broad s).

(3) 49 g of (Z)-2-(2-tritylaminothiazol-4-yl)-2-[(2-pyrrolidon-3-yl)oxyimino]acetic acid are suspended in a solution of one liter of methanol containing 40 ml of water, and the suspension is refluxed for 2 hours with heating. After cooling, crystalline precipitates are collected by filtration, and the crystals are washed with ethyl acetate. The crystals are recrystallized from a mixture of 500 ml of methanol and 50 ml of water, and dried at 70° C. under reduced pressure. 15.7 g of (Z)-2-(2-aminothiazol-4-yl)-2-[(2-pyrrolidon-3-yl)oxyimino]acetic acid are obtained as colorless prisms. The physico-chemical properties of this product are identical with those of the product obtained in Example 2-(4).

EXAMPLE 9

(1) 2.7 g of ethyl (Z)-2-(2-tritylaminothiazol-4-yl)-2-hydroxyiminoacetate are dissoved in 12 ml of dimethylsulfoxide, and 1.0 g of anhydrous potassium carbonate is added thereto under nitrogen gas atmosphere. The mixture is stirred at room temperature for 10 minutes. 1.2 g of 1-methyl-3-bromo-2-pyrrolidone are added to the mixture, and the mixture is stirred at room temperature for 5 hours. The reaction mixture is poured into 100 ml of water, and crystalline precipitates are collected by filtration. The crystals are dissolved in ethyl acetate, and the solution is washed with water and then dried. The solution is concentrated under reduced pressure to remove solvent. Then, the residue is crystallized with isopropyl ether and collected by filtration. 2.1 g of ethyl (Z)-2-(2-tritylaminothiazol-4-yl)-2-[(1-methyl-2-pyrrolidon-3-yl)oxyimin]acetate are obtained.

NMR (CDCl$_3$)$\delta$: 1.30 (3H, t, J=7 Hz), 2.0–2.7 (2H, m) 2.88 (3H, s), 3.0–3.6 (2H, m) 4.34 (2H, q, J=7 Hz), 4.92 (1H, t, J=7 Hz) 6.54 (1H, s), 6.87 (1H, s) 7.0–7.5 (15H, m).

(2) 2.7 g of ethyl (Z)-2-(2-tritylaminothiazol-4-yl)-2-[(1-methyl-2-pyrrolidon-3-yl)oxyimin]acetate are suspended in 27 ml of methanol, and 4.9 ml of 2N sodium hydroxide solution are added thereto. The mixture is refluxed for 20 minutes under heating. After cooling, the mixture is concentrated under reduced pressure to remove methanol. The residue is adjusted to pH 3 with 2N hydrochloric acid and extracted with ethyl acetate. The extract is dried and evaporated under reduced pressure to remove solvent. Then, the residue thus obtained is crystallized with ether and collected by filtration. 2.15 g of (Z)-2-(2-tritylaminothiazol-4-yl)-2-[(1-methyl-2-pyrrolidon-3-yl)oxyimino]acetic acid are obtained.

M.p. 142°–145° C. (decomp.).

NMR (DMSO-d$_6$)$\delta$: 2.0–2.5 (2H, m), 2.77 (3H, s) 3.1–3.4 (2H, m), 4.78 (1H, t, J=8 Hz) 6.87 (1H, s), 6.9–7.5 (16H, m).

EXAMPLE 10

1.3 g of (Z)-2-(2-tritylaminothiazol-4-yl)-2-hydroxyiminoacetic acid are dissolved in 10 ml of dimethylformamide, and 0.24 g of sodium hydride (60% oil dispersion) is added thereto. The mixture is stirred at room temperature for 15 minutes. 0.65 g of 3-bromo-2-piperidone is added to the mixture, and the mixture is stirred at room temperature for 1.5 hours. The reaction mixture is poured into water and washed with a mixture of ethyl acetate and tetrahydrofuran (1:1). The aqueous layer is adjusted to pH 3 with 10% hydrochloric acid and extracted with a mixture of ethyl acetate and tetrahydrofuran (1:1). The extract is dried and concentrated to dryness under reduced pressure. Then, ether is added to the residue, and the resulting powder is collected by filtration. The powder (1.3 g) is purified by silica gel chromatography (solvent, methanol:chloroform=1:4). 0.85 g of (Z)-2-(2-tritylaminothiazol-4-yl)-2-[(2-piperidon-3-yl)oxyimino]acetic acid are obtained.

M.p. 145°–150° C. (decomp.).

EXAMPLE 11

32.4 g of (Z)-2-(2-aminothiazol-4-yl)-2-[((3RS)-2-pyrrolidon-3-yl)oxyimino]acetic acid are suspended in 650 ml of methanol, and 19.5 g of L-tyrosine hydrazide are added thereto. The suspension is stirred under heating, and then refluxed for 15 minutes with heating. Then, the mixture is ice-cooled and allowed to stand. Crystalline precipitates are collected by filtration. The crystals are suspended in 480 ml of methanol, and the suspension is refluxed for 20 minutes. After cooling, the resulting crystals are collected by filtration and dried. 21.1 g of (Z)-2-(2-aminothiazol-4-yl)-2-[((3S)-2-pyrrolidon-3-yl)oxyimino]acetic acid.L-tyrosine hydrazide salt are obtained.

M.p. 167°–169° C. (decomp.).
[$\alpha$]$_D^{25}$: +24.1° (c=1, water).

21 g of the above-obtained salt are suspended in 90 ml of methanol, and 3.5 g of diethylamine are added thereto. The mixture is stirred at 45° to 55° C. for 30 minutes. The mixture is ice-cooled, and crystalline precipitates (L-tyrosine hydrazide) are filtered off. 4.9 ml of conc.-hydrochloric acid are added dropwise to the filtrate under ice-cooling, and crystalline precipitates are collected by filtration. The crystals are washed with methanol and dried. 11.3 g of (Z)-2-(2-aminothiazol-4-yl)-2-[((3S)-2-pyrrolidon-3-yl)oxyimino]acetic acid are obtained. The physico-chemical properties of this product are identical with those of the product obtained in Example 1-(3).

EXAMPLE 12

(1) 30 g of (Z)-2-(2-tritylaminothiazol-4-yl)-2-[((3RS)-2-pyrrolidon-3-yl)oxyimino]acetic acid and 60 ml of methanol are added to 100 ml of dioxane containing 10.5 g of L-phenylalanine methyl ester and the mixture is heated at 50° C. to dissolve said acid therein. 700 ml of dioxane are added to the solution, and the mixture is stirred at room temperature for 5 hours. Crystalline precipitates are collected by filtration (the filtrate is hereinafter referred to as "Filtrate I"), and 14.3 g of the crude product thus obtained are dissolved in 24 ml of methanol. 280 ml of dioxane are added to the methanol solution. The mixture is stirred at room temperature for 4 hours, and crystalline precipitates are collected by filtration (the filtrate is hereinafter referred to as "Filtrate II"). 12.2 g of (Z)-2-(2-tritylaminothiazol-4-yl)-2-[((3S)-2-pyrrolidon-3-yl)oxyimino]acetic acid.L-phenylalanine methyl ester salt are obtained.

[$\alpha$]$_D^{25}$: −14.0° (C=1, methanol).

12.2 g of the above-mentioned salt are dissolved in 120 ml of methanol, and 176 ml of 0.1N hydrochloric acid are added thereto. The mixture is stirred for 2 hours under ice-cooling. Crystalline precipitates are collected by filtration and washed with methanol. 7.5 g of (Z)-2-(2-tritylaminothiazol-4-yl)-2-[((3S)-2-pyrrolidon-3-yl)oxyimino]acetic acid are obtained.

M.p. 142°–143° C. (decomp.).
[$\alpha$]$_D^{25}$: −38.8° (C=1, dimethylformamide).

(2) Filtrate I and II obtained in the above mentioned paragraph (1) are condensed to dryness under reduced pressure. The residue is dissolved in 250 ml of methanol and then 450 ml of 0.1N hydrochloric acid are added dropwise to the solution. The mixture is stirred for 2 hours under ice-cooling. The resulting crystalline precipitates are collected by filtration, washed with methanol, and dried. 20 g of (Z)-2-(2-tritylaminothiazol-4-yl)-2-[(2-pyrrolidon-3-yl)oxyimino]acetic acid (containing excess of the R-isomer) are obtained. 20.0 g of (Z)-2-(2-tritylaminothiazol-4-yl)-2-[(2-pyrrolidon-3-yl)oxyimino]acetic acid thus recovered and 40 ml of methanol are added to 70 ml of dioxane containing 7.0 g of D-phenylalanine methyl ester, and the mixture is heated at 50° C. to dissolve said acid therein. 450 ml of dioxane are added to said solution. Then, the mixture is stirred at room temperature for 4 hours, and crystalline precipitates are collected by filtration. 13.3 g of the crude product thus obtained are dissolved in 20 ml of methanol, and 260 ml of dioxane are added thereto. The mixture is stirred at room temperature for 4 hours. Crystalline precipitates are collected by filtration. 12.0 g of (Z)-2(2-tritylaminothiazol-4-yl)-2-[((3R)-2-pyrrolidon- 3-yl)oxyimino]acetic acid.D-phenylalanine methyl ester salt are obtained.

$[\alpha]_D^{25}$: +13.9° (C=1, methanol).

12.0 g of the above-mentioned salt are dissolved in 120 ml of methanol, and 174 ml of 0.1N hydrochloric acid are added thereto. The mixture is stirred for 2 hours under ice-cooling. Crystalline precipitates are collected by filtration and washed with methanol. 7.3 g of (Z)-2-(2-tritylaminothiazol-4-yl)-2-[((3R)-2-pyrrolidon-3-yl)oxyimino]acetic acid are obtained.

M.p. 143°–144° C. (decomp.).

$[\alpha]_D^{25}$: +37.4° (C=1, dimethylformamide).

EXAMPLE 13

50 g of (Z)-2-(2-tritylaminothiazol-4-yl)-2-[((3RS)-2-pyrrolidon-3-yl)oxyimino]acetic acid are suspended in 320 ml of methanol, and 11.2 g of (+)-α-methylbenzylamine are added thereto. The mixture is stirred at room temperature for 17 hours. Crystaline precipitates are collected by filtration, and the crystals are washed with methanol and then air-dried at room temperature. 27.7 g of (Z)-2-(2-tritylaminothiazol-4-yl)-2-[((3S)-2-pyrrolidon-3-yl)oxyimino]acetic acid.(+)-α-methylbenzylamine salt trihydrate are obtained.

$[\alpha]_D^{25}$: −35.8° (C=1, dimethylformamide) (calculated for anhydrous compound.).

27.7 g of the above-obtained salt are suspended in 500 ml of methanol, and 810 ml of 0.05N hydrochloric acid are gradually added dropwise to the suspension. The mixture is stirred at 5° C. for 5 hours. Crystalline precipitates are collected by filtration, and the crystals are air-dried at room temperature. 21.6 g of (Z)-2-(2-tritylaminothiazol-4-yl)-2-[((3S)-2-pyrrolidon-3-yl)oxyimino]acetic acid dihydrate are obtained.

M.p. 144°–146° C. (decomp.).

$[\alpha]_D^{25}$: −37.3° (C=1, dimethylformamide) (calculated for anhydrous compound).

EXAMPLE 14

40 g of (Z)-2-(2-tritylaminothiazol-4-yl)-2-[((3RS)-2-pyrrolidon-3-yl)oxyimino]acetic acid are suspended in 260 ml of methanol, and 9.0 g of (−)-α-methylbenzylamine are added thereto. The mixture is stirred at room temperature for 16 hours. Crystalline precipitates are collected by filtration, and the crystals are air-dried at room temperature. 22.3 g of (Z)-2-(2-tritylaminothiazol-4-yl)-2-[((3R)-2-pyrrolidon-3yl)oxyimino]acetic acid.(−)-α-methylbenzylamine salt trihydrate are obtained.

$[\alpha]_D^{25}$: +35.6° (C=1, dimethylformamide) (calculated for anhydrous compound).

22.0 g of the above-obtained salt are suspended in 400 ml of methanol, and 650 ml of 0.05N hyrochloric acid are gradually added dropwise to the suspension at about 40° C. After the addition, the mixture is stirred at 5° C. for 2 hours. Crystalline precipitates are collected by filtration, and the crystals are air-dried at room temperature. 17.3 g of (Z)-2-(2-tritylaminothiazol-4-yl)-2-[((3R)-2-pyrrolidon-3-yl)oxyimino]acetic acid dihydrate are obtained.

M.p. 144°–145° C. (decomp.).

$[\alpha]_D^{25}$: +38.0° (C=1, dimethylformamide) (calculated for anhydrous compound).

EXAMPLES 15 TO 24

The following compounds may be obtained in the same manner as described in Examples 1 to 5.

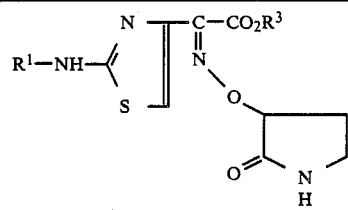

| Ex. Nos. | $R^1$ | $R^3$ | Optical isomer | Physico-chemical properties |
|---|---|---|---|---|
| 15 | H | H | R | M.P. 198–200° C. (decomp.) <br> $[\alpha]_D^{25}$ + 50.5° (C = 1, water) |
| 16 | HCO | $C_2H_5$ | RS | M.p. 184–188° C. (decomp.) <br> NMR (DMSO-$d_6$)δ: <br> 1.30 (3H, t, J = 7Hz), 1.9–2.4 (2H, m) <br> 3.1–3.4 (2H, m), 4.40 (2H, q, J = 7Hz), <br> 4.83 (1H, t, J = 7Hz), 7.61 (1H, s), <br> 8.00 (1H, broad s), 8.57 (1H, s) |
| 17 | " | H | " | M.p. 191–193° C. <br> NMR (DMSO-$d_6$)δ: <br> 2.0–2.5 (1H, m), 3.1–3.5 (2H, m), <br> 4.83 (1H, t, J=7Hz), 7.59 (1H, s), <br> 8.02 (1H, s), 8.59 (1H, s), 11.35 (1H, s) |
| 18 | $CH_3CO$ | " | S | M.p. 122–123° C. (decomp.) <br> $[\alpha]_D^{25}$ −21.5° (C = 1, methanol) <br> NMR (DMSO-$d_6$)δ: <br> 2.0–2.5 (2H, m) 2.15 (3H, s), <br> 3.1–3.5 (2H, m), 4.83 (1H, t, J = 7Hz), <br> 7.52 (1H, s), 8.03 (1H, broad s), <br> 12.5 (1H, broad s) |
| 19 | $CH_3$ | H | R | M.p. 121–123° C. (decomp.) <br> $[\alpha]_D^{25}$ + 20.9° (C =1, methanol) <br> NMR (DMSO-$d_6$)δ: <br> 2.05–2.5 (2H, m), 2.16 (3H, s), <br> 3.1–3.5 (2H, m), 4.84 (1H, t, J = 7Hz), <br> 7.52 (1H, s), 8.00 (1H, s), <br> 12.5 (1H, broad s) |
| 20 | $ClCH_2CO$ | $C_2H_5$ | RS | M.p. 120–123° C. |

-continued

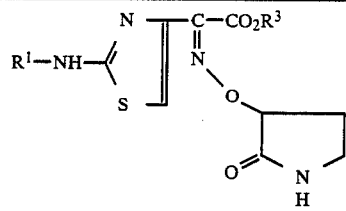

| Ex. Nos. | R¹ | R³ | Optical isomer | Physico-chemical properties |
|---|---|---|---|---|
| | | | | NMR (DMSO-d₆)δ: 1.30 (3H, t, J = 7Hz), 2.0 2.5 (2H, m), 3.1–3.5 (2H, m), 4.40 (2H, q, J = 7Hz), 4.42 (2H, s), 4.83 (1H, t, J = 7Hz), 7.63 (1H, s), 8.01 (1H, s), 12.90 (1H, broad s) |
| 21 | " | H | " | M.p. 192° C. (decomp.) NMR (DMSO-d₆)δ: 1.9–2.4 (2H, m), 3.1–3.5 (2H, m) 4.40 (2H, s), 4.81 (1H, t, J = 7Hz), 7.57 (1H, s), 8.00 (1H, s) 12.93 (1H, broad s) |
| 22 | " | " | S | M.p. 190–191° C. (decomp.) $[\alpha]_D^{25}$ − 34.2° (C = 1, dimethyldormamide) NMR (DMSO-d₆)δ: 2.0–2.5 (2H, m), 3.1–3.4 (2H, m), 4.41 (2H, s), 4.83 (1H, t, J = 7Hz), 7.60 (1H, s), 8.01 (1H, s), 12.95 (1H, broad s) |
| 23 | ClCH₂CO | H | R | M.p. 189–191° C. (decomp.) $[\alpha]_D^{25}$ + 33.9° (C = 1, dimethylformamide) NMR (DMSO-d₆)δ: 1.95–2.5 (2H, m), 3.1–3.4 (2H, m), 4.40 (2H, s), 4.83 (1H, t, J = 7Hz), 7.59 (1H, s), 8.00 (1H, s), 12.93 (1H, broad s) |
| 24 | Cbz | " | RS | M.p. 160–170° C. (decomp.) NMR (DMSO-d₆)δ: 2.0–2.4 (2H, m), 3.0–3.5 (2H, m) 4.70 (1H, t, J = 7Hz), 5.24 (2H, s) 7.29 (1H, s), 7.43 (5H, s), 8.29 (1H, broad s) | note:
Cbz: Benzyloxycarbonyl

Preparation of Starting Compound 2 g of (R)-3-hydroxy-2-pyrrolidone (Acta Chemica Scandinavica: B34 (1980) 731–733) are suspended in 30 ml of acetone, and 15 ml of 2N sodium hyroxide are added thereto at room temperature to dissolve said pyrrolidone therein. The solution is cooled to −3° to 5° C., and 5.7 g of p-toluenesulfonyl chloride are added thereto. The mixture is stirred at the same temperature for one hour, and further stirred at 10° to 15° C. overnight. The mixture is adjusted to pH 2 with about 10 ml of 2N hydrochloric acid, and the mixture is concentrated under reduced pressure to remove acetone. The aqueous mixture thus obtained is extracted with chloroform, and the extract is washed with a saturated sodium chloride solution. The chloroform solution is dried and concentrated under reduced pressure to remove solvent. The residue is crystallized with ether, and the crystals are recrystallized from ethyl acetate. 3.5 g of (R)-3-(p-tosyloxy)-2-pyrrolidone are obtained.

M.p. 148°–149° C.

$[\alpha]_D^{25}$: +17.7° (C=1, methanol).

NMR (CDCl₃)δ: 2.0–2.7 (2H, m), 2.43 (3H, s), 3.1–3.5 (2H, m), 4.91 (1H, t, J=7 Hz) 7.2 (1H, br), 7.32 (2H, d, J=9 Hz). 7.84 (2H, d, J=9 Hz).

REFERENCE EXAMPLE 1.81 g of oxalyl chloride are added at 5° to 0° C. to 45 ml of chloroform containing 1.15 ml of dimethylformamide, and the mixture is stirred at the same temperature for 15 minutes. A solution of 4.90 g of (Z)-2-(2-tritylaminothiazol-4-yl)-2-[((3S)-2-pyrrolidon-3-yl)oxyimino]acetic acid and 0.97 g of triethylamine in 45 ml of chloroform is added to said mixture at −30° C. The mixture is stirred at the same temperature for 5 minutes. Then, a solution of (6R, 7R)-7-amino-3-(1-pyridiniomethyl)-3-cephem-4-carboxylate in chloroform (said solution is prepared by suspending 5.8 g of the dihydrochloride of said cephem compound in 45 ml of chloroform and adding 12.7 ml of N,O-bis(trimethylsilyl)acetamide thereto to dissolve said salt therein) is added to the mixture at −30° to −10° C. After the mixture is stirred at the same temperature for 30 minutes, said mixture is concentrated to dryness under reduced pressure. 100 ml of 80% aqueous formic acid are added to the residue, and the aqueous mixture is stirred at room temperature for one hours. 110 ml of water are added to the mixture, and insoluble materials are filtered off. The filtrate is washed with ethyl acetate and is concentrated to dryness under reduced pressure. The residue thus obtained is dissolved in water and chromatographed on a column of non-ionic polymer resin Diaion HP-20 (resistered trade mark, manufactured by Mitsubish Chemical Industries Ltd., Japan). The column is washed with water, followed by elution with 20% aqueous methanol. The franctions containing the cephalosporin compound are collected and concentrated to dryness under reduced pressure. Acetone is added to the residue, and the resulting powder is collected by filtration. 2.22 g of (6R, 7R)-7-{(Z)-2-(2-aminothiazol-4-yl)-2-[((3S)-2-pyrrolidon-3-yl)oxyimino]acetamido}-3-(1-pyridiniomethyl)-3-cephem-4-carboxylate are obtained.

NMR (D$_2$O)δ: 2.2–2.7 (2H, m), 3.1–3.8 (4H, m) 5.05 (1H, t, J=7 Hz), 5.28 (1H, d, J=5 Hz), 5.36 (1H, d, J=14 Hz), 5.63 (1H, d, J=14 Hz), 5.87 (1H, d, J=5 Hz), 6.98 (1H, s), 8.10 (2H, t, J=7.5 Hz), 8.57 (1H, t, J=7.5 Hz), 8.98 (2H, d, J=7.5 Hz).

$[\alpha]_D^{20}$: −38.0° (C=1, H$_2$O).

Experiment I (Antimicrobial activity in vitro)

The minimum inhibitory concentration (MIC, μg/ml) of a test compound was determined by means of standard agar plate dilution method (based on the standard method of Japan Society of Chemotherapy). Media used in these experiments were Mueller-Hinton agar (MHA; Nissui).

The results are shown in the following Table 1.

TABLE 1

| Microorganisms tested | M.I.C. (μg/ml) | | |
|---|---|---|---|
| | The compound prepared in Reference example (Note: 1) | Cefmenoxime (Note: 2) | Ceftazidime (Note: 3) |
| Staphylococcus aureus Terajima | 0.78 | 1.56 | 12.5 |
| Staphylococcus aureus 252R | 25 | >100 | >100 |
| Streptococcus faecalis CN-478 | 12.5 | >100 | >100 |
| Bacillus subtilis ATCC 6633 | 0.2 | 1.56 | 3.13 |
| Klebsiella pneumoniae 5038 | 0.05 | 0.1 | 0.1 |
| Enterobacter cloacae TU-680 | ≦0.05 | 0.1 | 0.2 |
| Serratia marcescens 7006 | ≦0.05 | 0.2 | 0.2 |
| Pseudomonas aeruginosa 4096 | 0.39 | 6.25 | 0.78 |
| Pseudomonas putida ATCC 12633 | 1.56 | 100 | 12.5 |

Note:
(1): (6R,7R)—{(Z)—2-(2-aminothiazol-4-yl)-2-[((3S)—2-pyrrolidon-3-yl)-oxyimino]acetamido}-3-(1-pyridiniomethyl)-3-cephem-4-carboxylate
(2): Chemical name = 7β-[(Z)—2-(2-aminothiazol-4-yl)-2-methoxyimino)acetamido]-3-[(1-methyl-1H—tetrazol-5-yl)-thiomethyl]-3-cephem-4-carboxylic acid
(3): Chemical name = 7β-[(Z)—2-(2-aminothiazol-4-yl)-2-(2-carboxy-prop-2-yloxyimino)acetamido]-3-(1-pyridiniomethyl)-3-cephem-4-carboxylate Experiment II (Protective effects on bacterial infections in mice)

Ten male mice weighing 20±1 g were used for each dose level. Mice were challenged via the intraperitoneal route with sufficient bacteria to kill all non-treated mice within 24 hours. All bacteria were suspended in 6% mucin. A test compound were administered intramuscularly one hour after the infection. Survival ratios were determined 7 days after the infection. The median effective doses (ED$_{50}$, mg/kg) of the test compound was estimated by the probito analysis.

The results are shown in the following Table 2 together with the M. I. C. (μg/ml) of the test compound which was estimated in the same manner as described in Experiment I.

TABLE 2*

| Microorganisms tested | ED$_{50}$ (mg/kg) | | |
|---|---|---|---|
| | The compound prepared in Reference example (Note: 1) | Cefmenoxime (Note: 2) | Ceftazidime (Note: 3) |
| Staphylococcus aureus Smith | 1.71 (1.56) | 5.32 (1.56) | 7.85 (12.5) |
| Escherichia coli KC-14 | 0.05 (0.05) | 0.16 (0.025) | 0.08 (0.05) |
| Serratia marcescens 7006 | 0.14 (0.05) | 0.88 (0.2) | 0.54 (0.2) |
| Citrobacter freundii 916 | 0.06 (0.1) | 0.19 (0.05) | 0.15 (0.39) |
| Enterobacter aerogenes 816 | 1.37 (0.39) | 23.85 (1.56) | 26.38 (6.25) |

Note:
*the numerical values in parenthesises show the M. I. C. (minimum inhibitory concentration, μg/ml) of each test compounds.
(1)–(3): same as shown in the footnote of Table 1.

What we claim is:
1. A compound of the formula:

$$R^1NH-\underset{S}{\overset{N}{\diagdown}}\!\!\!\!\!-\!\!\!\!\!\underset{}{\overset{C-COOR^3}{\underset{N}{\|}}}\!\!\!-O-CH(CH_2)_n-N(R^2)-C=O$$ (I)

wherein R$^1$NH— is amino or a protected amino group, R$^2$ is hydrogen or lower alkyl, —COOR$^3$ is carboxy or a protected carboxy group and n is an integer of 2 or 3, or a salt thereof.

2. The compound claimed in claim 1 which is (Z)-2-(2-aminothiazol-4-yl)-2-[(2-pyrrolidon-3-yl)oxyimino]acetic acid or a salt thereof.

3. The compound claimed in claim 1 which is (Z)-2-(2-aminothiazol-4-yl)-2-[((3S)-2-pyrrolidon-3-yl)oxyimino]acetic acid or a salt thereof.

4. The compound claimed in claim 1, in which R$^1$ is hydrogen, formyl, lower alkanoyl, mono-, di- or trihalogeno-lower alkanoyl, lower alkoxycarbonyl, mono-, di- or trihalogeno-lower alkoxycarbonyl, benzyloxycarbonyl, p-methoxybenzyloxycarbonyl, phenyl-lower alkyl, p-methoxyphenyl-lower alkyl, 3,4-dimethoxyphenyl-lower alkyl, or di-or triphenyl-lower alkyl, or R$^3$ is hydrogen, lower alkyl, phenyl-lower alkyl, p-methoxyphenyl-lower alkyl, p-nitrophenyl-lower alkyl or benzhydryl.

5. The compound claimed in claim 1, in which R$^1$ is acetyl, pivaloyl, chloroacetyl, trifluoroacetyl, methoxy carbonyl, ethoxycarbonyl, tert.-butoxycarbonyl, 2,2,2-trichloroethoxycarbonyl, p-methoxybenzyloxycarbonyl, benzyl, p-methoxybenzyl, 3,4-dimethoxybenzyl, benzhydryl or trityl; or R$^3$ is benzyl, p-methoxybenzyl or p-nitrobenzyl.

6. The compound claimed in claim 1, in which R$^2$ or R$^3$ is methyl, ethyl or propyl.

7. The compound claimed in claim 1, in which R$^1$, R$^2$ and R$^3$ are each hydrogen and n is 2.

8. The compound claimed in claim 1, in which the configuration of the oxyimino group is Z-configuration and the configuration of the asymmetric carbon atom is S-configuration.

* * * * *